United States Patent [19]

McCormack

[11] 4,454,360
[45] Jun. 12, 1984

[54] PREPARATION OF PARA-NITROBENZOTRICHLORIDE

[75] Inventor: William B. McCormack, Wilmington, Del.

[73] Assignee: E. I. Du Pont de Nemours and Company, Wilmington, Del.

[21] Appl. No.: 445,895

[22] Filed: Dec. 1, 1982

[51] Int. Cl.³ .......................................... C07C 79/12
[52] U.S. Cl. ................................................. 568/936
[58] Field of Search ...................................... 568/936

[56] References Cited

U.S. PATENT DOCUMENTS 4,098,831 7/1978 Marsh ................................. 568/936
4,393,257 7/1983 Nakagawa et al. ................. 568/936

OTHER PUBLICATIONS

Puri et al., Indian J. Chem. vol. 19A, pp. 109-112, Feb. 1980.
Puri et al. Indian J. Chem. vol. 16A, pp. 1026-1029, Dec. 1978.

Primary Examiner—Leland A. Sebastian

[57] ABSTRACT

Para-nitrobenzotrichloride is prepared by chlorinating nitrotoluene using an activated carbon catalyst. The process can use various cocatalysts such as bromine, iodine, PCl₃, S₂Cl₂, bromide salts, chloranil, air bubbles and phthalimide. The reaction is carried out at from 20° C., to 220° C., with from 150° to 200° C. being the preferred range and a pressure of 1 to 5 Atm.

3 Claims, 3 Drawing Figures

PNT + DARCO G-60 SPECIAL (5g) + $Cl_2$ AT 180°

PNT + DARCO G-60 SPECIAL (5g) + 0.5ml Br₂ + Cl₂ AT 180°

PREPARATION OF PARA-NITROBENZOTRICHLORIDE

BACKGROUND OF THE INVENTION

1. Field of the Invention

The present invention relates to the chlorination of para-nitrotoluene.

2. Prior Art

Puri et al., Indian J. Chem., Vol. 19A, pp 109–112, February 1980 discloses the chlorination of toluene to form benzyl chloride.

Puri et al., Indian J. Chem., Vol. 16A, pp 1026–1029, December 1978 discloses preparing benzyl chloride, at 250° to 400° C., from toluene using an activated carbon catalyst.

SUMMARY OF THE INVENTION

The present invention relates to the side chain chlorination of para-nitrotoluene to form para-nitrobenzotrichloride (PNT) using chlorine gas and an activated carbon catalyst.

DETAILED DESCRIPTION

Figure 1:
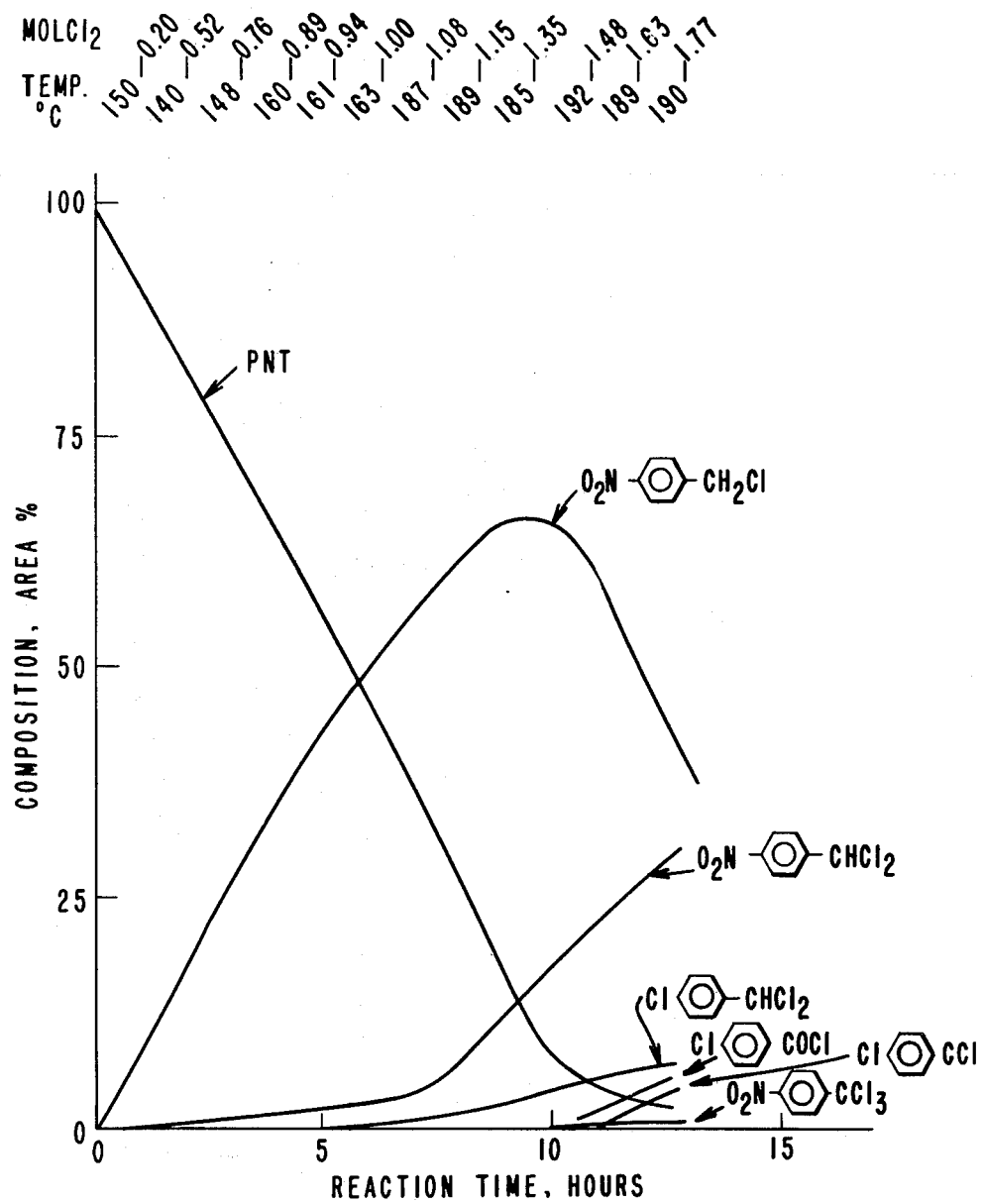
FIGS. 1–3 are plots showing the progress of the chlorination of para-nitrotoluene in Examples 1–3.

The present invention relates to a process for preparing para-nitrobenzotrichloride. Para-nitrobenzoltrichloride is useful as an intermediate for preparing para-aminobenzotrifluoride. Para-aminobenzotrifluoride is an intermediate in preparing the insecticide 1 5-bis-(4 trifluoromethyl phenyl)-3-formazancarbonitrile as disclosed in U.S. Pat. No. 4,069,320.

The reactions of chlorine with para-nitrotoluene are as follows:

Above 200° C. and especially above 220° C. chlorinolysis becomes the dominate reaction. Below 150° C. and especially below 120° C. the reaction becomes unduly slow.

Generally a pressure of 1 to 5 Atm is used. Below 1 Atm the reaction rate becomes unduly slow. Pressures above 5 Atm promote undesired side reactions.

The reaction times used are fairly long since the reaction proceeds in three steps and the last step has a fairly slow reaction rate. However excessively long reaction times are to be avoided because side reactions such as the chlorinolysis of the nitro group on para-nitrobenzotrichloride to form para-chlorobenzotrichloride begin to become excessive. Generally the reaction time will be from 2 to 20 hours. The particular reaction time used depends on the particular activated carbon catalyst used, the temperature used and what if any cocatalyst is used. These same factors also affect the products' distribution.

The activated carbon catalyst generally will have a surface area of from 500 to 1500 $m^2/g$. Generally the activated carbons prepared from wood, coconut husk, or sugar are preferred for use in the present invention, although other active carbon sources such as acetylene black can be used. Generally from 1 to 10 g of catalyst per mole of para-nitrotoluene are used.

The reaction rate can be increased by using a cocatalyst. Generally the cocatalyst is a catalyst for the chlorination of organic compounds. Suitable cocatalysts include bromine; iodine; salts of bromine or iodine with cesium, platinum, copper, mercury, gold or tetra lower alkyl quaternary ammonium compounds; $S_2Cl_2$; $PCl_3$; chloranil; air bubbles phthalimide; and chlorophthalimide.

EXAMPLES

General Procedure

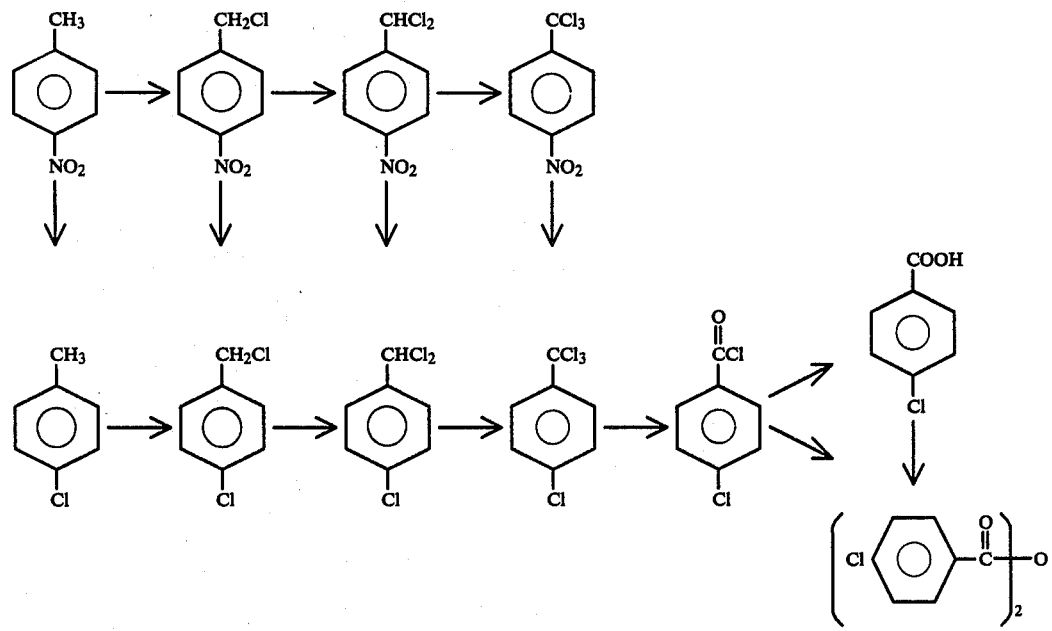

The para-chlorobenzotrichloride can readily be converted to para-chlorobenzotrifluoride which is a commercial product.

The reaction is carried out at from 120° to 220° C. with from 150° C. to 200° C. being the preferred range.

A reaction vessel consisting of a 4-necked flask is fitted with a chlorine gas feed tube as a sparger, stirrer, thermometer and air condenser. Chlorine feed is from a feed cylinder on a balance, via a bubbler and flowmeter with protective traps and a vent system if overpressure develops. The vent gases, after passing through intermediate protective traps, pass through, first, a dry ice cooled trap to remove most of the excess chlorine and other high boiling gases, and then through a water absorber system to remove HCl.

Charging is carried out by adding 1.00 mol PNT to the cold flask, then usually the catalyst components, and the mixture heated. In some runs lasting several days, additional catalyst is added each morning. When the para-nitrotoluene (PNT) melts agitation is started, and heating continued until the desired reaction temperature is reached, usually in about 15 min. Temperature is regulated by a control system. When the desired temperature is reached, chlorine feed is started, and regulated to give a constant ratio of conversion. The procedure used is to measure the depth of liquid chlorine in the vent side dry-ice cooled trap, and control $Cl_2$ feed so as to give a constant rate of accumulation in the trap.

The chemical changes in the reaction mix are followed by periodically taking a sample. If solid is present the sample is filtered, with solution with methylene chloride as necessary. A portion of the filtrate is injected into a gas chromatography (GC) column for determination of area percent composition of volatile components, using a silicone separating agent.

When a run is terminated the cooled mixture is taken up in methylene chloride and then filtered to remove insoluble material. Removal of the methylene chloride then gives a crude organic product which on cooling to room temperature usually solidifies in part. A composition of volatile components of this final crude is determined.

Chemical composition of product and the course of the reaction in Examples 1-3 is assayed by plotting the composition in area percent, determined from the gas chromatography column (GC) results, against the reaction time in hours. The usual products seen are reported in FIGS. 1-3. Not all products are plotted in all runs. 4-Chlorotoluene and 4-chlorobenzyl chloride are usually low in amount (<5%) and disappear as reaction proceeds. Not all values for products plotted are reported since low values can overlap on the figure and confuse the plot.

The activated carbon used in the Examples was a commercial catalyst support activated carbon prepared from a carbohydrate source having a surface area of 900 $m^2/g$ as measured with iodine and an average particle size of 25 microns with 70 percent of the particles passing through a 325 mesh per inch screen.

EXAMPLE 1

A base run without catalyst was carried out by passing chlorine into 0.365 mol (50 g.) of PNT at temperatures of 150°-190° C. for thirteen hours. Following the product mix by (GC) analysis gave the results shown in FIG. 1. At most, less than 1% of the desired 1-nitro-4-trichloromethylbenzene was formed. Loss of nitro group was a dominant process as a side reaction.

EXAMPLE 2

Figure 2:
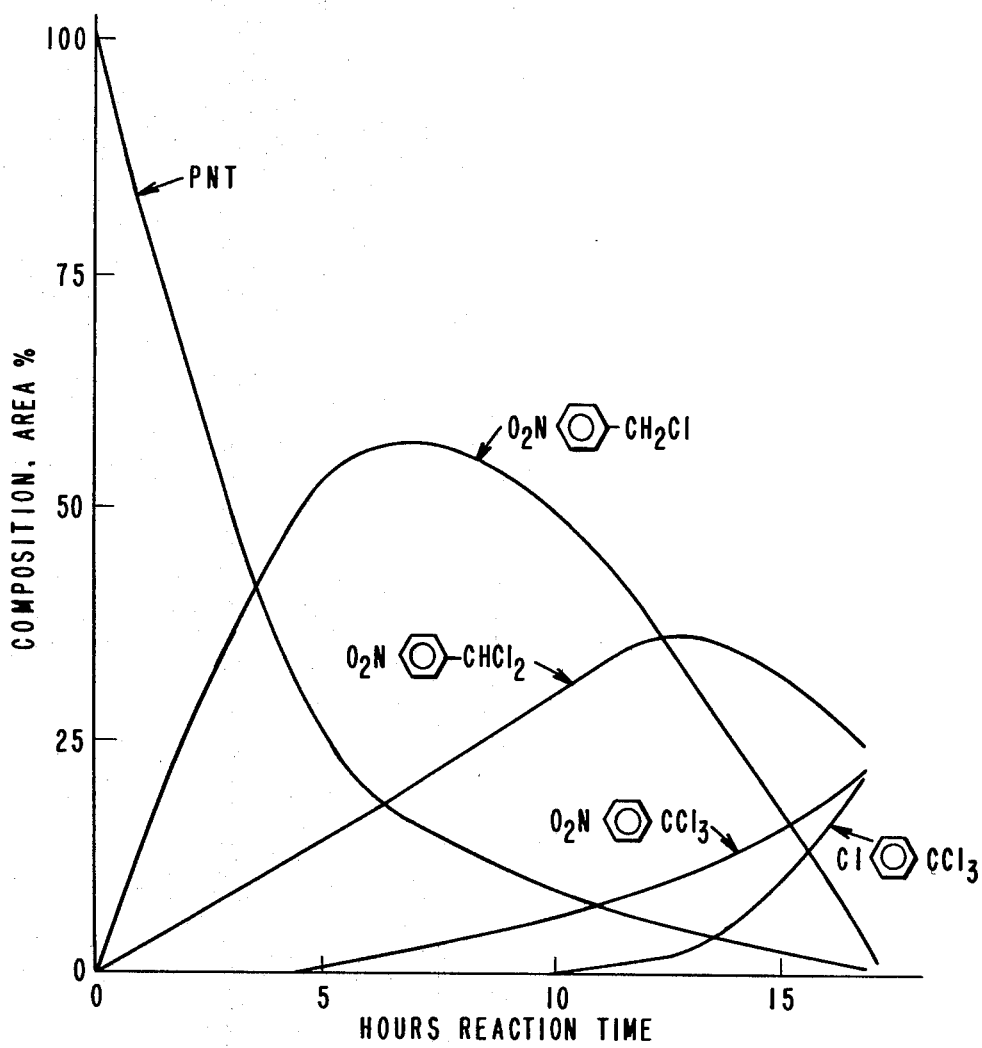

When 5 g of an active charcoal is added to the charge and chlorination carried out at a temperature of 180° C. for 17 hours, results shown in FIG. 2 are obtained. Compared to Example 1, the PNT reacts faster, the resulting mono- and dichlorinated products form faster, and the desired trichloro product is present in appreciable amounts at 13 hours.

EXAMPLE 3

Figure 3:
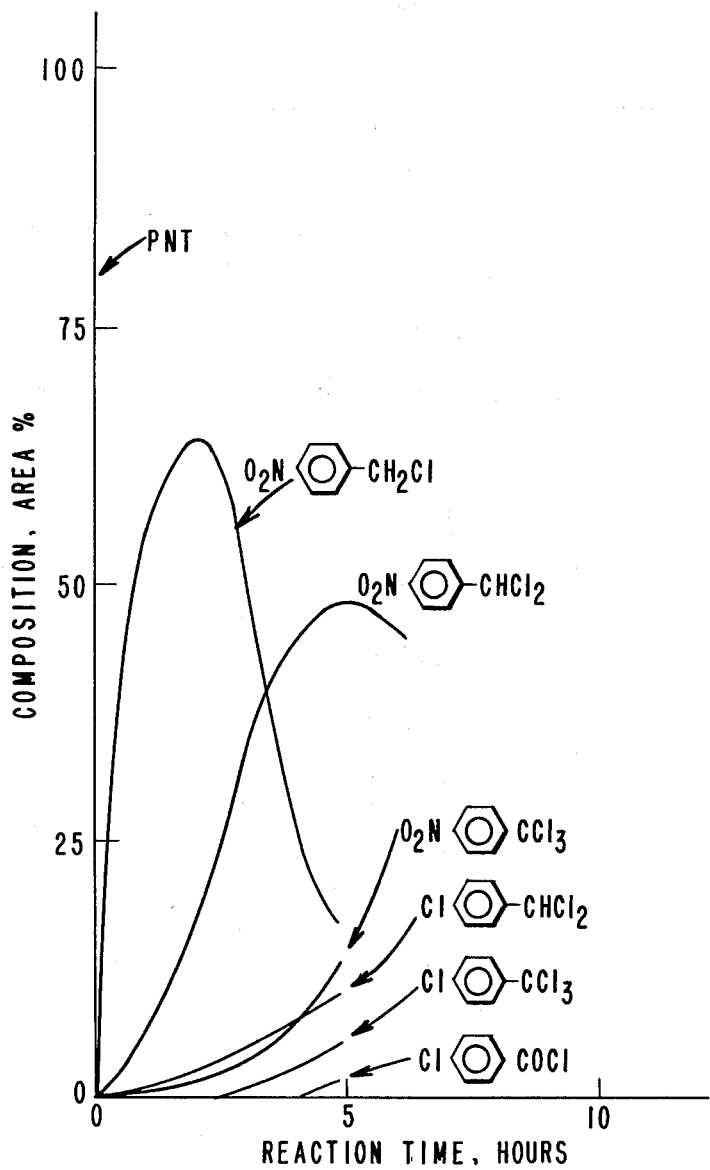

When 5 g of the active charcoal and 0.5 ml of bromine are added to the charge and chlorination carried out at a temperature of 180° C. for 4.8 hours, results shown in FIG. 3 are obtained. Compared with Examples 1 and 2, reaction of PNT is faster still, being all reacted by 5 hours. The mono- and dichloro products form much faster, and the desired trichloro product is present in appreciable amounts in 5 hours.

EXAMPLES 4-25

A number of experiments were run to examine the catalytic effect of carbon addition, and the cocatalyst effect of other compounds known to be catalysts for chlorination. Results of the experiments are presented in Table I, using 1.0 mol PNT in each run. Multiple addition of catalytic agents are indicated where used. Rates are summarized in disappearance rate for PNT, and times to peak concentration for the mono- and dichloro PNT. Product is area product by (GC) for volatile product in the final organic crude. The net $CH_2Cl_2$ insoluble is the weight of material insoluble in the methylene chloride diluted crude, after subtracting the weight of carbon added.

A number of comparisons show the value of carbon as catalyst and of cocatalysts with carbon in producing the desired chlorination. In Examples 2, 11 and 12, 5 g of active carbon at several temperatures produced more trichloronitro compound than in Example 1 with no carbon. Results were best at 180° C. in this comparison, with a higher temperature causing much chlorinolysis and formation of acid chloride and a lower temperature giving a reduced rate. In Examples 3-7, various combinations of amount of carbon, temperature, amount of bromine and carbon pre-mixed with bromine were employed. Reaction rates with a carbon/bromine combination increased over that for carbon alone (Examples 2, 11 and 12) or for bromine alone (Example 7). Other sources of bromine as tetrabutylammonium bromide (Example 8) or cesium bromide (Example 9) were comparable to elemental bromine in effect. Iodine acted as a cocatalyst (Example 10). Several metal salts, of copper, mercury, gold and platinum, which will modify chlorinating by themselves, enhanced the effect of carbon (Example 13). The use of bromine along with $PtCl_2$ on carbon further increased the rate (Example 25 vs. Example 15). Other agents that promote oxidations and halogenations enhanced the effect of carbon, including $PCl_3$ (Example 17), air (Examples 20 and 21), $S_2Cl_2$ (Example 22) and chloranil (Example 18). Chloranil with carbon was faster than with carbon alone (Example 18 vs. 2) or with chloranil alone (Example 18 vs. 19). Phthalimide, as a representative of the materials giving catalytically active chlorimides, greatly increased the rate of chlorination when used with carbon (Example 23 vs. Example 2), and was faster than phthalimide alone (Example 23 vs. 24), although phthalimide alone showed some catalytic effect (Example 24 vs. Example 1).

TABLE I
CATALYTIC EFFECT OF ACTIVE CARBON ON CHLORINATION OF PNT

| Ex. | Catalyst Solid - g | Catalyst Other - g | Temp., °C. | Total React. Time - Hrs. | Conversion of PNT Hrs. 70% | 90% | 95% | Final Cl ⌬-CH$_2$Cl | Crude Cl ⌬-COCl | Org. Cl ⌬-CHCl$_2$ | -Vol. Cl ⌬-CCl$_3$ | -Comp. O$_2$N-⌬-CH$_2$Cl | -Area O$_2$N-⌬-CHCl$_2$ | % O$_2$N-⌬-CCl$_3$ |
|---|---|---|---|---|---|---|---|---|---|---|---|---|---|---|
| 1 | — | — | 150° 190° | 13.0 | 7.7 | 9.6 | 11.1 | 7 | 6 | 7 | 5 | 40 | 31 | 0.7 |
| 2 | C - 5 g | — | 180° | 17.0 | 4.5 | 9.5 | 12.5 | — | 10 | 15 | 24 | 3 | 23 | 24 |
| 3 | C - 5 g | Br$_2$ - 0.5 ml | 180° | 4.8 | 1.0 | 2.2 | 3.0 | 2 | 3 | 12 | 5 | 15 | 48 | 14 |
| 4 | C - 5 g | Br$_2$ - 5 ml | 180° | 6.2 | 0.4 | 0.8 | 1.2 | 0.1 | 7 | 10 | 40 | 0.1 | 15 | 28 |
| 5 | C - 5 g | Br$_2$ - 0.5 ml | 150° | 6.5 | 3.0 | 5.5 | 6.8 | 4 | — | 5 | 0.4 | 54 | 28 | 1 |
| 6 | C - 5 +5 g | Br$_2$ - 5 + 5 ml | 150° | 12.9 | 1.8 | 2.3 | 4.2 | — | 0.5 | 3 | 8 | 0.1 | 52 | 35 |
| 7 | — | Br$_2$ - 5 × 1 ml | 180° | 12.4 | 2.0 | 4.0 | 5.2 | — | 64 | 2 | 7 | 4 | 4 | 7 |
| 8 | C - 5 g | Bu$_4$N$^+$Br 1.0 g | 180° | 5.5 | 1.3 | 2.5 | 3.2 | 0.6 | 6 | 27 | 22 | 1 | 21 | 21 |
| 9 | C - 5 g | CsBr - 1.0 g | 180° | 6.3 | 1.5 | 2.5 | 3.4 | 1 | 8 | 22 | 23 | 2 | 24 | 16 |
| 10 | C - 5 g | I$_2$ - 0.3 g | 180° | 12.1 | 3.6 | 5.5 | 6.5 | 1 | 12 | 17 | 20 | 1 | 26 | 20 |
| 11 | C - 5 g | — | 150° | 12 | 6.5 | 10.5 | 12 | 8 | 0 | 9 | 0.4 | 44 | 30 | 1 |
| 12 | C - 5 +5 g | — | 190° | 16.3 | 4.8 | 8.0 | 9.5 | 0.2 | 21 | — | 71 | — | 1 | 3 |
| 13 | 1% CuCl$_2$ on C - 5 g | — | 150° | 13.1 | 4.5 | 9.0 | 10.5 | 5 | 0.4 | 6 | 0.5 | 48 | 31 | 4 |
| 14 | 1% AuCl$_3$ on C - 5 g | — | 180° | 9.3 | 3.5 | 5.5 | 6.5 | 2 | 5 | 14 | 14 | 6 | 32 | 25 |
| 15 | 1% PtCl$_2$ on C - 5 g | — | 180° | 8.6 | 1.8 | 3.6 | 4.5 | — | 10 | 16 | 32 | 1 | 14 | 25 |
| 16 | 1% HgCl$_2$ on C - 5 g | — | 180° | 11.1 | 3.5 | 5.5 | 6.5 | 0.6 | 6 | 13 | 39 | 0.3 | 11 | 29 |
| 17 | C - 5 g | PCl$_3$ - 2 ml | 180° | 10.2 | 2.5 | 4.6 | 5.6 | 1 | 31 | 18 | 3 | 0.2 | 25 | 9 |
| 18 | C - 5 +5 g | Chloranil - 1 + 1 g | 180° | 9.6 | 1.9 | 2.6 | 3.0 | 0.7 | 14 | 6 | 47 | 1 | 3 | 23 |
| 19 | — | Chloranil - 1 g | 180° | 5.8 | 2.0 | 4.2 | 5.5 | 6 | 3.5 | 3.5 | 0.2 | 49 | 30 | 1 |
| 20 | C - 5 g | Air-Bubble | 180° | 6.4 | 1.2 | 2.0 | 2.7 | 0.7 | 7 | 17 | 28 | 1 | 22 | 23 |
| 21 | C - 5 g | Air-Bubble | 150° | 19.2 | 3.0 | 6.5 | 11 | 1 | 2 | 10 | 8 | 13 | 42 | 24 |
| 22 | C - 5 g | S$_2$Cl$_2$ - 1 ml | 180° | 6.3 | 1.8 | 2.7 | 3.2 | 1.5 | 8 | 13 | 14 | 4 | 34 | 23 |
| 23 | C - 5 +5 g | Phthalimide 2 + 2 g | 180° | 12.8 | 1.6 | 3.2 | 5.0 | — | 18 | 0.6 | 71 | — | 0.1 | 5 |
| 24 | — | Phthalimide 2 g | 180° | 6.3 | 1.6 | 3.2 | 5.5 | 7 | 4 | 3 | — | 43 | 38 | 1 |
| 25 | 1% PtCl$_2$ on C - 5 g | Br$_2$ - 2 ml | 180° | 8.3 | 1.4 | 2.0 | 3.2 | — | 5 | 5 | 59 | — | 4 | 26 |

I claim:

1. A process for preparing para-nitrobenzotrichloride from para-nitrotoluene comprising contacting para-nitrotoluene with chlorine gas for from about 2 to about 20 hours, at a temperature of from about 120° C. to about 220° C., and a pressure of from about 1 to about 5 atmospheres in the presence of a catalytic amount of activated carbon, and recovering para-nitrobenzotrichloride.

2. The process of claim 1 wherein the activated carbon has a surface area of from about 500 m$^2$/g to about 1500 m$^2$/g.

3. The process of claim 2 wherein a cocatalyst selected from the group consisting of bromine, iodine, PCl$_3$, S$_2$Cl$_2$, bromide salts, chloranil, air bubbles, and phthalimide.

* * * * *